(12) United States Patent
Ries et al.

(10) Patent No.: US 8,267,937 B2
(45) Date of Patent: Sep. 18, 2012

(54) METHOD FOR DETERMINING A TOOTH PERIOD LENGTH OF A BONE MILLING CUTTER

(75) Inventors: Wolfgang Ries, Linkenheim (DE); Mathias Notheis, Forst (DE)

(73) Assignee: Joimax GmbH, Karlshure (DE)

( * ) Notice: Subject to any disclaimer, the term of this patent is extended or adjusted under 35 U.S.C. 154(b) by 1407 days.

(21) Appl. No.: 11/898,231

(22) Filed: Sep. 11, 2007

(65) Prior Publication Data
US 2008/0077148 A1 Mar. 27, 2008

(30) Foreign Application Priority Data
Sep. 27, 2006 (DE) .......................... 10 2006 045 508

(51) Int. Cl.
*A61B 17/00* (2006.01)

(52) U.S. Cl. ............................... 606/79; 606/80; 76/115

(58) Field of Classification Search .................... 606/80; 29/407.01, 407.05; 76/115
See application file for complete search history.

(56) References Cited

U.S. PATENT DOCUMENTS

| 5,759,185 | A | 6/1998 | Grinberg | |
| 6,588,992 | B2* | 7/2003 | Rudolph | ........................ 408/204 |
| 6,682,535 | B2 | 1/2004 | Hoogland | |
| 2006/0008771 | A1 | 1/2006 | Courvolsier | |

FOREIGN PATENT DOCUMENTS

| DE | 699 17 683 | 7/2005 |
| DE | 202005016762 | 1/2007 |
| DE | 202005016763 | 1/2007 |
| EP | 0 296 986 | 12/1988 |

* cited by examiner

*Primary Examiner* — Andrew Yang
(74) *Attorney, Agent, or Firm* — McGlew and Tuttle, P.C.

(57) ABSTRACT

A method for manufacturing bone milling cutters, wherein a milling cutter toothing (12) is created at a distal face of a tubular milling cutter shaft (10) of a bone milling cutter at a given outer diameter (D) of the milling cutter shaft (10). The following steps are carried out: determining the tube circumference (U) of the milling cutter shaft (10); ascertaining an average desired tooth height (Hgew) of the milling cutter toothing (12); ascertaining the desired tooth period length (LZ') of the milling cutter toothing from the desired tooth height (Hgew) at given parameters of a tooth period pattern; dividing the tube circumference (U) by the desired tooth period length (LZ); rounding the results to an even number value (Qz); and dividing the tube circumference (U) by the value (Qz) in order to obtain the tooth period length (LZ).

20 Claims, 4 Drawing Sheets

METHOD FOR DETERMINING A TOOTH PERIOD LENGTH OF A BONE MILLING CUTTER

This application claims Paris Convention priority of DE 10 2006 045 508.8 filed Sep. 27, 2006 the complete disclosure of which is hereby incorporated by reference.

BACKGROUND OF THE INVENTION

The invention relates to a method for manufacturing bone milling cutters, wherein a milling cutter toothing is created at a distal face of a tubular milling cutter shaft of a bone milling cutter at a given outer diameter of the milling cutter shaft as well as to a device for manufacturing bone milling cutters with which a milling cutter toothing is created at a digital face of a tubular milling cutter shaft of a tubular milling cutter shaft of a bone milling cutter at a given outer diameter of the milling cutter shaft. The invention further relates to a bone milling cutter with a tubular milling cutter shaft and a milling cutter toothing at a distal face of the tubular milling cutter shaft, wherein the milling cutter toothing is formed from a number of tooth period patterns periodically distributed over at least a part of a tube circumference of the milling cutter shaft.

A conventional a bone milling cutter, for example from DE 699 17 683 T2, has a hollow cylindrical milling cutter shaft, a handle at its rear, proximal end and a milling cutter toothing at its front or distal end.

Such a milling cutter is employed in the field of medical technology to mill out vertebra components in the area of a lateral process of a spine vertebra in order to establish postero-lateral access to pinched nerve roots of the central nervous system. Nucleus propulsus tissue and other tissue types (capsule tissue, scar tissue, annulus tissue) are then removed through this access because they press on the nerve roots. The specified process of a vertebra forms, together with an adjacent process of an adjacent vertebra, the so-called facet joint.

The micro invasive operation method, which employs a generic facet joint milling cutter and which is for decompressing pinched nerve roots, is highly successful. Due to the high sensitivity of such an intervention, generic bone milling cutters must be made in an extremely precise manner and must have a high degree of toughness in order to avoid blunting of the toothing. Furthermore, such a bone-milling cutter must be stable during use and must not slip under any circumstances. All of these requirements must be fulfilled with the ability to disinfect both simply and well. For this reason, the manufacture of bone milling cutters of the generic type, which is additionally carried out in small numbers, is very expensive. In particular, this is important because a surgeon generally does not need only one bone milling cutter, but rather a whole range with various dimensions and toothing patterns.

Departing from this prior art, the invention has the objective of creating a method for manufacturing a bone-milling cutter in which the manufacturing cost is reduced compared to milling cutter toothings, which are dimensioned in accordance with the known method while avoiding the stated disadvantages. Moreover, the method should facilitate dimensioning of a milling cutter such that good stability and toughness of the toothing is ensured during use of the bone-milling cutter.

SUMMARY OF THE INVENTION

According to the invention, the object is achieved with a method of the generic type, which is characterized by the following steps:

- determining the tube circumference of the milling cutter shaft;
- ascertaining an average desired tooth height of the milling cutter toothing;
- ascertaining the desired tooth period length of the milling cutter toothing from the desired tooth height at given parameters of a tooth period pattern;
- dividing the tube circumference by the desired tooth period length;
- rounding the results to an even number value;
- dividing the tube circumference by the value in order to obtain the tooth period length.

The method according to the invention can be particularly advantageously implemented in a device for manufacturing a bone milling cutter which is configured in accordance with the invention and in which the dimensioning of bone milling cutters, made individually or in small production runs, can be calculated automatically using the method according to the invention depending on few parameters, for example the tooth height, and can flow directly into the manufacturing process.

Finally, the object of the invention is solved by a bone milling cutter in which the number of the tooth period patterns is an even number and/or in which at least one pair of tooth period patterns is arranged point-symmetrically with regard to a center line of the tubular milling cutter shaft.

By selecting an even-number value for the number of the tooth period patterns distributed over the tube circumference, there can be achieved, in particular in the case of a simple tooth period pattern, in a particularly simple manner, a paired point-symmetrical arrangement of the tooth period patterns which strongly simplifies manufacture and thereby makes it less expensive. Opposing tooth period patterns can be processed simultaneously, while guaranteeing a radial course of cutting edges.

Herein, "length" refers to the extension of the tooth period pattern or of an individual tooth in the circumference direction of the milling cutter shaft, while the term "height" refers to the axial direction of the milling cutter shaft.

Instead of directly involving the circumference of the tube, the outer diameter of the tube can be specified as a parameter, with the tube circumference then being determined from the outer diameter of the milling cutter shaft. For example, a radius can be specified instead of the outer diameter. The outer diameter or a parameter that is proportional thereto can, for example, be read in and set from a database or by a user interface.

Ascertaining an average desired tooth height of the milling cutter toothing can also be carried out by reading-in from a database or using a user interface.

According to a particularly advantageous embodiment of the method according to the invention, an adaptation, in particular a scaling of the tooth height or an adaptation of the wedge angle and/or angle of incidence of the tooth period pattern can, after ascertaining the tooth period length, be carried out in order to set the ascertained tooth period length in an advantageous proportion to the tooth height. Thus, in certain circumstances, small deviations of the ultimate tooth height from the desired tooth height, as well as deviations of the ultimate ascertained tooth shape from the desired tooth shape, as determined by the given parameters of the tooth period pattern, can be tolerated.

A possible design of the above-defined device according to the invention allows for the parameters for the tooth period pattern to comprise at least one wedge angle and/or one angle of incidence. As both the cutting characteristics and the height/length ratios of a saw tooth are largely determined by these angles, they form particularly significant parameters.

If the tooth period pattern contains at least one pair of teeth, wherein a fraction of the tooth period length is advantageously formed in order to determine the length of at least one tooth of the tooth period pattern and/or wherein, in particular, a fraction of the tooth height is formed in order to determine the height of at least one tooth of the tooth period pattern, the method according to the invention can be generalized simply from individual teeth to more complex teeth period patterns.

If the height of the larger tooth and the height of the smaller tooth are determined starting from a common tooth tip line, substantial stability of the larger teeth can be achieved with highly effective material removal. Therefore, bone-milling cutters of this type with medium-sized double teeth are particularly suitable for precise work with good tooth stability and good removal of material.

A disadvantageous alteration of the length relationship between the smaller tooth and the larger tooth can be avoided if the length of at least one larger and one smaller tooth of the tooth period pattern is determined such that the proportions do not move due to the variation in length of an individual tooth.

A bone milling cutter which is particularly well dimensioned for precise working with good teeth stability and good material removal can be achieved by the method according to the invention if, when ascertaining the desired tooth period length from the tooth height of the milling cutter toothing, the length of the larger tooth of the tooth period pattern is determined such that it is ⅔ of the tooth height, with the length of the smaller tooth of the tooth period pattern being determined such that it is ⅓ of the tooth height, wherein the tooth period length corresponds to the sum of the lengths of the teeth.

In order to achieve a bone milling cutter, in particular one with rough toothing, which is particularly suitable for the largest degree of effectiveness in removing material with good teeth stability, it is proposed that the height of the larger tooth and the height of the smaller tooth be determined starting from a common tooth base line. The effectiveness in the case of material removal arises from the fact that, as a result of this dimensioning, the smaller teeth remain hidden below the tooth tip line of the larger teeth.

Surprisingly, it was discovered that the effectiveness in the case of high stability is particularly high if, when ascertaining the desired tooth period length from the tooth height of the milling cutter toothing, the length of the larger tooth of the tooth period pattern is determined such that it is ⅗ of the tooth height and that the length of the smaller tooth of the tooth period pattern is determined such that it is ⅖ of the tooth height, wherein the tooth period length corresponds to the sum of the lengths of the teeth.

The milling cutter is normally made of stainless steel. Preferably, the toothing is configured in that the toothing is configured at the distal tube end by means of mechanical removing or severing of material, with the toothing in particular being created by laser welding. Alternatively, other methods such as grinding, milling or etching can be employed.

Further advantages and features of the invention arise from the claims and from the subsequent description in which embodiments of the invention are explained in detail. In the figures:

DESCRIPTION OF THE PREFERRED EMBODIMENT

Figure 1:
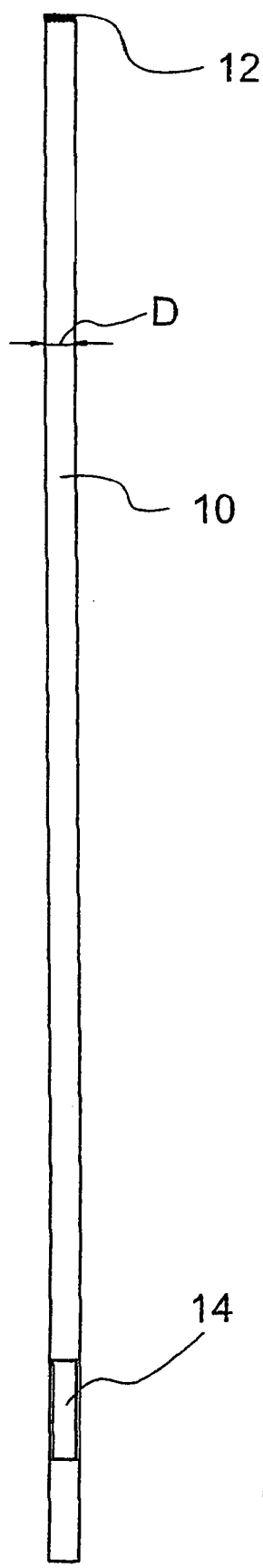
FIG. 1 shows a bone-milling cutter with a milling cutter toothing.

FIG. 1 shows a bone milling cutter which has a hollow cylindrical milling cutter shaft 10, a handle, which is not depicted here, at its rear proximal end and a milling cutter toothing 12 of a first type at its front or distal end. The milling cutter shaft 10 has, at its proximal end, a recess 14 for fixing the handle.

Such a bone-milling cutter is employed in the field of medical technology to mill out vertebra components in the area of a lateral process of a spine vertebra in order to establish a postero-lateral access to pinched nerve roots of the central nervous system.

Figure 2:
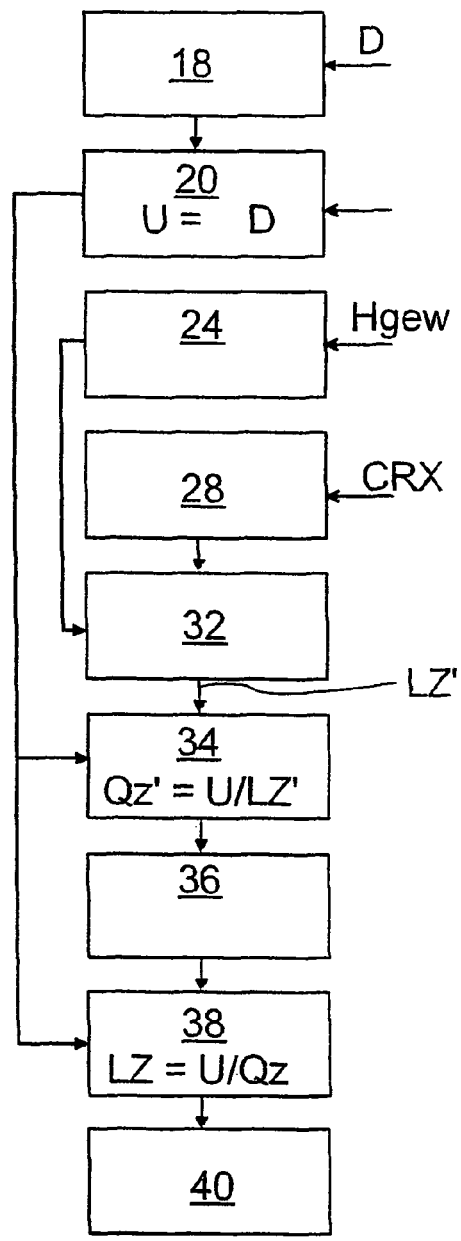
FIG. 2 shows a flow chart of a method for determining a tooth period length of a milling cutter toothing.

The bone milling cutter depicted in FIG. 1 is the direct product of a manufacturing method which, alongside known processing steps, in which, in the case of known sizes of bone milling cutters, this is made from a metal tube, comprises a method for determining the dimensions of the bone milling cutter, as is depicted in FIG. 2. In the latter method, there is determined in particular a tooth period length LZ of a milling cutter toothing 12 at a distal face of a tubular milling cutter shaft 10 of the bone milling cutter, in the case of a given outer diameter D of the milling cutter shaft 10.

The method steps illustrated in FIG. 2 are thereby carried out.

In a first step 18, the outer diameter D from a calculation unit which is not depicted here and which controls the method is read in from a database or a user interface.

In a first calculating step 20, the calculation unit calculates the tube circumference U from the outer diameter D of the milling cutter shaft 10 by multiplying the outer diameter D by the number 0 which it reads in from read-only memory.

Subsequently, the calculation unit ascertains, in a step 24, an average desired tooth height Hgew of the milling cutter toothing 12 by reading in this value, which is supplied by an operator.

Furthermore, the calculation unit ascertains in a toothing type ascertaining step 28 with which of 5 different toothing types CRX. CRX refers to a variable, which codes the toothing type with which the bone-milling cutter to be produced should be equipped. The variable CRX can assume values CRX=CRF, CRM, CRC, CRP or CRPF. The toothing types CRX are explained further below (FIGS. 4-8).

Subsequently, the calculation unit ascertains a target value for the tooth period length LZ' in a length determination step 32 from the desired tooth height Hgew ascertained in the step and depending on the toothing type CRX which is coded by given parameters of a tooth period pattern.

In a dividing step 34, the calculating unit divides the tube circumference U by the desired tooth period length LZ' or the target value and, in a rounding step 36, rounds the result to an even-number value Qz.

Finally, in a second dividing step 38, the calculating unit divides the tube circumference U by the value Qz in order to obtain the tooth period length LZ.

After ascertaining the tooth period length LZ, a scaling of the actual tooth height H takes place in an adaptation step 40 through the ratio consisting of the desired tooth period length LZ' and the actual tooth period length LZ obtained in the second dividing step 38. By means of the scaling, it is achieved that the wedge angle a and/or angle of incidence c of the tooth period pattern are independent from the desired tooth height Hgew.

By selecting an even-number value Qz for the number of the tooth period patterns distributed over the tube circumference U, a paired point-symmetrical arrangement of the individual tooth period patterns is achieved in a particularly simple manner which greatly simplifies manufacture and therefore makes it less expensive. Opposing tooth period patterns can be processed simultaneously, wherein a radial course of cutting edges can be guaranteed.

In advantageous embodiments, there arise for the value Qz even numbers between 6 and 30 in the case of outer diameters D between 2 and 9.5 mm.

The parameters for the tooth period pattern comprise, for example, a wedge angle a and/or an angle of incidence c. Therefore, in the length determination step 32, the tooth length or tooth period length LZ can be determined by simple trigonometric calculations, since the projection of the tooth flanks on the circumference direction of the milling cutter shaft 10 can be calculated simply by multiplying the desired tooth height Hgew by the inverse cosine of the corresponding angle. Of course, instead of the angles, it is also possible to directly store the inverse cosine or another suitable trigonometric function as a parameter.

FIGS. 3-8 show concrete embodiments with different tooth period patterns. The subsequent description is limited to those differences in the method for determining the tooth period length LZ which arise from the different tooth period patterns, while, in view of the constant features, reference is made to the above general description of the method.

A device according to the invention is configured for carrying out the thus-specified steps and for creating the suitable toothing at a shaft.

Figure 3:
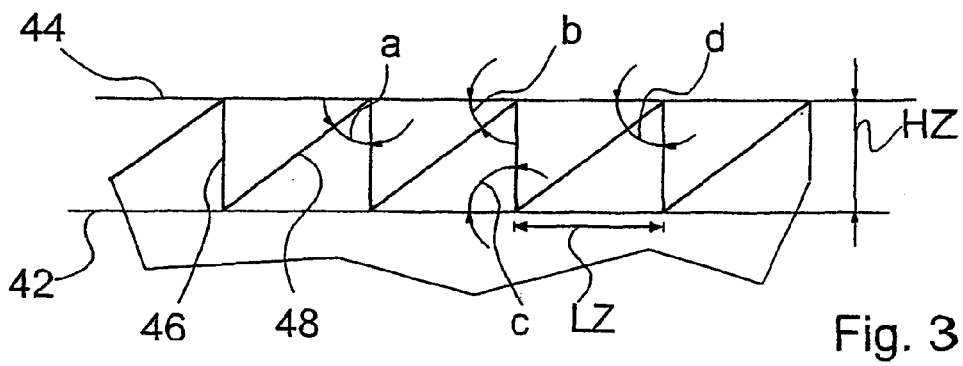
FIG. 3 shows a detail from a milling cutter toothing for illustrating parameters of the tooth period pattern.
Figure 4:
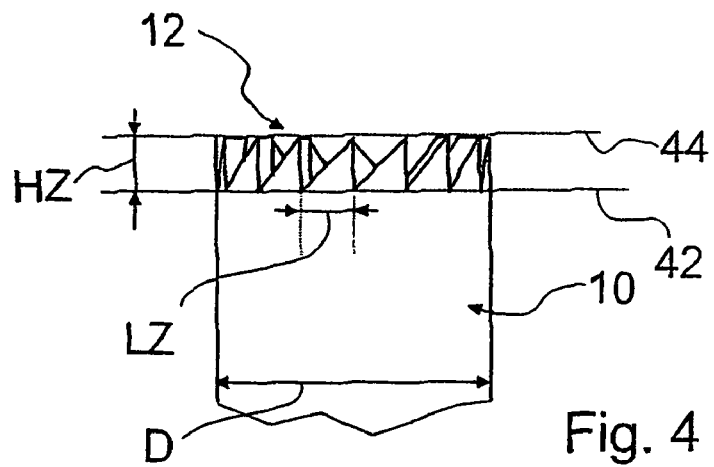
FIG. 4 shows a distal end of a bone-milling cutter with a milling cutter toothing of a CRF toothing type.

FIG. 3 shows a detail from a milling cutter toothing 12 with a simple tooth period pattern of the type 30=CRF with only one tooth. The tooth has a wedge angle a of 45° and an angle of incidence c of 90°. The distal end, which is depicted in FIG. 4, of a bone-milling cutter is equipped with the milling cutter toothing 12, which is depicted in FIG. 3. This is particularly suitable for fine works shortly before the end of the operation where efficiency in terms of material removal is of lesser importance compared to the required precision.

In the example from FIGS. 3 and 4, the length determination step 32 turns out to be particularly simple because, due to the wedge angle s of 45°, the tooth period length LZ is identical to the desired tooth height Hgew, such that the two values can simply be equalized. For the toothing type CRX=CRF, the intersecting angle is d=90° and the clearance angle is b=45°.

In general, the parameters of the tooth period pattern are angles between a pair of characteristic straight lines of the tooth period pattern. The characteristic straight lines are, in particular, the tooth base line 42, the tooth tip line 44, the cutting tooth face 46 and the tooth back 48, wherein, in the case of several teeth in a tooth period pattern, different angles can also be assigned to the cutting tooth faces 46 and the tooth backs 48. The interior angle between the cutting tooth face 46 and the tooth back 48 is also referred to as wedge angle a, the interior angle between the tooth base line 42 and the cutting tooth face 46 is referred to as angle of incidence c, the angle between the tooth back 48 and the tooth tip line 44 is referred to as clearance angle b and the angle between the tooth tip line 44 and the cutting tooth face 46 is referred to as intersecting angle d.

Figure 5:
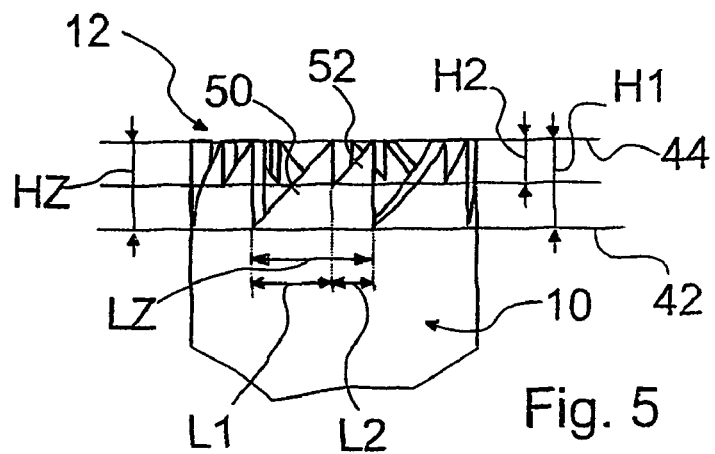
FIG. 5 shows a distal end of a bone-milling cutter with a milling cutter toothing of a CRM toothing type.
Figure 6:
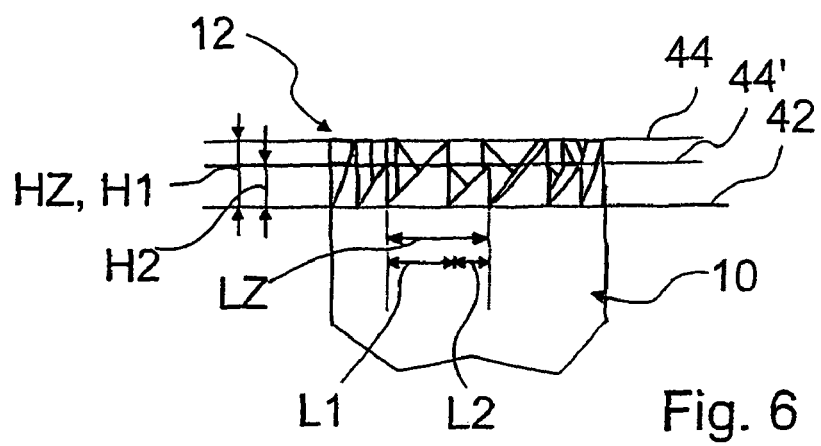
FIG. 6 shows a distal end of a bone-milling cutter with a milling cutter toothing of a CRC toothing type.

If the tooth period pattern contains at least one pair of teeth, as is the case with toothing types depicted in FIGS. 5 and 6, the calculation unit forms, in the length determination step 32, a fraction of the desired tooth height Hgew in order to determine the height and length of at least one tooth of the tooth period pattern.

In the embodiment depicted in FIG. 5 of the toothing type CRX=CRM, the length L1 of the larger tooth 50 of the tooth period pattern is determined in length determination step 32, when ascertaining the desired tooth period length LZ from the desired tooth height Hgew of the milling cutter toothing 12, such that it is ⅔ of the tooth height Hgew and the length L2 of the smaller tooth 52 of the tooth period pattern is determined such that it is ⅓ of the tooth height Hgew. The wedge angle a of the teeth 50, 52 is 45° and the angle of incidence c is 90°. The toothing type CRX=CRM is designed for precise work with a large degree of stability of the teeth 50, 52 and good removal of the material. In the length determining step 32, both the length L2 of the smaller tooth 52 and the length L1 of the larger tooth 50 is determined proportional to the desired tooth height Hgew such that the proportions are set independently of the desired tooth height Hgew, wherein the tooth period length LZ always corresponds to the sum of the lengths L1, L2 of the teeth 50, 52.

The vertical arrangement of the two teeth 50, 52 of the tooth period pattern of the CRM type is chosen such that the height H1 of the larger tooth 50 and the height H2 of the smaller tooth 52 are determined starting from a common tooth tip line 44. Bone milling cutters of this type with medium-sized double teeth are thus particularly suitable for precise working with good stability of the teeth 50, 52 and good removal of material.

In advantageous embodiments of bone milling cutters with tooth period patterns of the CRM type, there arise for the value Qz numbers between 2 and 9 in the case of outer diameters D between 2 and 9.5 mm. The length of the small tooth 52 is then between 1.0472 mm and 1.1054 mm and the length of the larger tooth 50 is then between 2.0944 mm and 2.2108 mm.

A bone milling cutter, which is particularly well dimensioned for a high degree of material removal, is achieved by means of the toothing type CRX=CRC which is depicted in FIG. 6. Bone milling cutters with the toothing type CRX=CRC are particularly suitable for rough preliminary work in which a larger amount of material needs to be removed and in which precision is of secondary importance. In the length determination step 32, when ascertaining the desired tooth period length LZ from the tooth height Hgew of the milling cutter toothing 12, length L1 of the larger tooth 50 of the tooth period pattern is determined such that it is ⅗ of the desired tooth height Hgew and such that the length L2 of the smaller tooth 52 of the tooth period pattern is determined such that it is ⅖ of the tooth height Hgew, wherein the tooth period length LZ corresponds to the sum of the lengths L1, L2 of the teeth 50, 52.

In a bone milling cutter of the toothing type CRX=CRC, the height H1 of the larger tooth 50 and the height H2 of the smaller tooth 52 is determined starting from a common tooth base line 42 such that the tooth tip line 44' of the smaller teeth 52 is situated under the tooth tip line 44 of the larger teeth 50. The effectiveness in terms of material removal arises from the fact that, as a result of this dimensioning, the smaller teeth 52 remain hidden below the tooth tip line 44 of the larger teeth 50.

Figure 7:
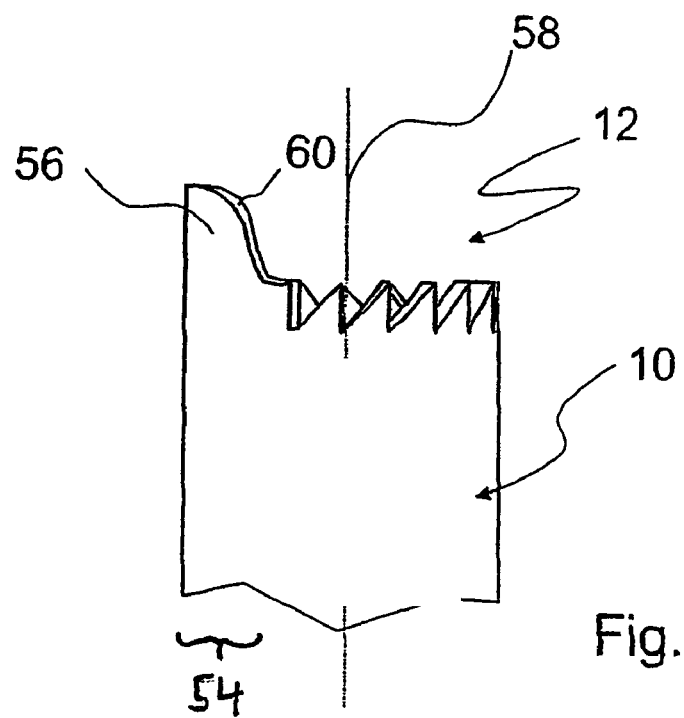
FIG. 7 shows a distal end of a bone milling cutter with a milling cutter toothing of a CRP toothing type.

FIG. 7 shows a bone milling cutter with a milling cutter toothing 12 of the tooth type CRX=CRP. This toothing type is characterized in that the milling cutter toothing 12 does not extend over the entire circumference of the face of the milling cutter shaft 10 but rather discontinues in a sector 54 in which there is provided a protector lip 56 which axially protrudes over the milling cutter toothing 12. The protector lip 56 extends over an angle area which can, in principle, be freely selected but is normally situated between 90° and 180° such that, in any case, a pair of tooth periods is point-symmetrical with regard to the center line 58 of the tubular milling cutter shaft 10. The point-symmetry relates to the axial plan view.

Such a bone-milling cutter can be employed to protect tissue arranged beside the bone to be processed and to avoid injuries. Besides, the milling cutter toothing 12 in the bone-milling cutter depicted in FIG. 7 matches that of toothing type CRM.

Figure 8:
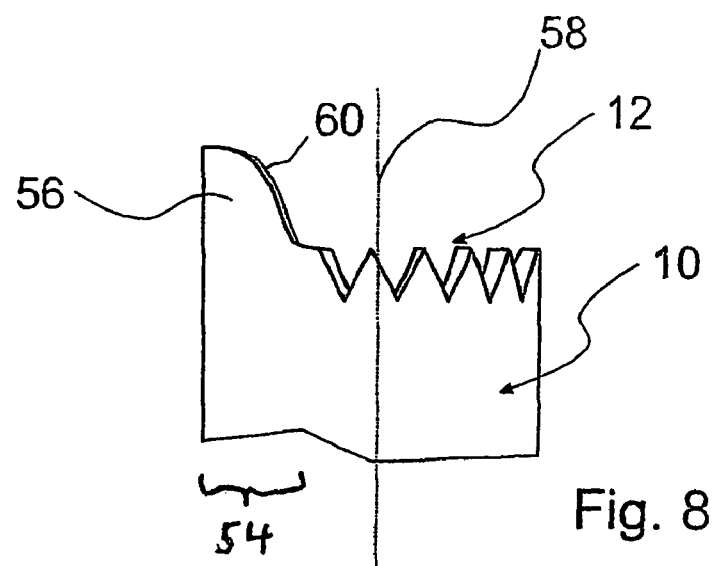
FIG. 8 shows a distal end of a bone-milling cutter with a milling cutter toothing of a CRPF toothing type.

FIG. 8 shows a bone milling cutter with a milling cutter toothing 12 of the toothing type CRX=CRPF. Like the toothing type CRX=CRP, this toothing type has a protector lip with a front rasp 60. However, the toothing in the area of the distal front, which completes the protector lip into a circle, corresponds to a toothing type with isosceles teeth for working on impact.

Independent of the selection of the toothing type CRX, the result of the above-described manufacturing method is a bone milling cutter with a tubular milling cutter shaft 10 and a milling cutter toothing 12 at a distal face of the tubular milling cutter shaft 10, wherein the milling cutter toothing 12 is formed by a number of tooth period patterns periodically distributed over at least a part of a tube circumference U of the milling cutter shaft 10. The characteristic of the bone milling cutter is that at least a pair of tooth period patterns is arranged point-symmetrically with regard to a center line 58 of the tubular milling cutter shaft 10 because the number Uzi of tooth period patterns is an even number.

As is also the case for the toothing type CRX=CRF, the intersecting angle d is 90° and the clearance angle b is 45° in the toothing types CRM, CRC, CRP and CRPF. In order to generalize the method according to the invention to other toothing types in which the angle of incidence c deviates from 90°, the tooth lengths can be ascertained in the length determination step 32 simply by the desired tooth height Hgew and using the trigonometric functions. Toothing types, with which it is possible to work on impact (angle of incidence c<90°) or on pulling (angle of incidence c>90°), can thus also be achieved.

The above-described methods may obviously also be employed for dimensioning further tooth period patterns which appear sensible to the person skilled in the art, for example for those with a curved cutting tooth face or for those with more than two teeth. Furthermore, the methods are not limited to bone milling cutters with a purely cylindrical milling cutter shaft 10 but may also be employed in conjunction with milling cutter shafts which expand radially in the area of the milling cutter toothing 12 or below the milling cutter toothing 12.

LIST OF REFERENCE NUMERALS

10 milling cutter shaft
12 milling cutter toothing
14 recess
18 step
20 calculating step
24 step
28 toothing type ascertaining step
32 length determination step
34 dividing step
36 rounding step
38 dividing step
40 adapting step
42 tooth base line
44 tooth tip line
46 cutting tooth face
48 tooth back
50 tooth
52 tooth
54 sector
56 protector lip
58 center line
60 rasp
a wedge angle
b clearance angle
c angle of incidence
d intersecting angle
L1 length
L2 length
H1 height
H2 height
Hgew, HZ tooth height
LZ, LZ' tooth period length
U tube circumference
D outer diameter
Qz value
CRX toothing type

We claim:

1. A method for manufacturing a bone milling cutter, the method comprising:
    providing a tubular milling cutter shaft;
    determining a tube circumference of the milling cutter shaft;
    determining an average desired tooth height of the milling cutter toothing after determining said tube circumference of the milling cutter shaft;
    determining a desired tooth period length of the milling cutter toothing from the desired tooth height at given parameters for a tooth period pattern after determining said average desired tooth height of said milling cutter toothing;
    dividing the tube circumference by the desired tooth period length to form a divided result and rounding said divided result to an even number value after determining said desired tooth period length of the milling cutter toothing;
    dividing the tube circumference by the even number value after dividing the tube circumference by the desired tooth period length to obtain an actual tooth period length; and
    mechanically removing or severing material to form a plurality of teeth at a distal end of the milling cutter shaft via one of laser cutting, grinding, milling and etching based on said actual tooth period length after obtaining said actual tooth period length, each of said teeth comprising said desired tooth period length of said milling cutter toothing.

2. The method of claim 1, wherein a height of a larger tooth and a height of a smaller tooth are determined starting from a common tooth base line.

3. A method in accordance with claim 1, wherein a height of at least one larger and one smaller tooth of the tooth period pattern is determined, wherein the height of the larger tooth and the height of the smaller tooth are determined starting from a common tooth tip line.

4. A method in accordance with claim 1, wherein a protector lip extends in a circumferential direction at said distal end of said milling cutter shaft, said protector lip extending between one of said plurality of teeth and another one of said plurality of teeth, said protector lip extending in an axial direction of said milling cutter shaft, said protector lip having an end portion, said end portion being located at a spaced location from each of said plurality of teeth in said axial direction.

5. A method of claim 1, wherein, when determining the desired tooth period length from the desired tooth height of the milling cutter toothing, a length of the larger tooth of the tooth period pattern is determined such that the length of the larger tooth is ⅔ of a tooth height and a length of the smaller tooth of the tooth period pattern is determined such that the length of the smaller tooth is ⅓ of a tooth height, wherein the tooth period length corresponds to a sum of lengths of the teeth.

6. A method for manufacturing a bone milling cutter, the method comprising:
providing a cutting device;
providing a tubular milling cutter shaft;
determining a tube circumference of the milling cutter shaft;
determining an average desired tooth height of the milling cutter toothing after determining said tube circumference of the milling cutter shaft;
determining a desired tooth period length of the milling cutter toothing from the desired tooth height at given parameters for a tooth period pattern after determining said average desired tooth height of said milling cutter toothing;
dividing the tube circumference by the desired tooth period length to provide a quotient and rounding said quotient to an even number value after determining said desired tooth period length of the milling cutter toothing;
dividing the tube circumference by the even number value to obtain an actual tooth period length after dividing the tube circumference by the desired tooth period length; and
forming a plurality of teeth at a distal end of said milling cutter shaft by cutting material at said distal end of said milling cutter shaft with said cutting device based on said actual tooth period length after obtaining said actual tooth period length.

7. A method in accordance with claim 6, wherein said cutting includes one of laser cutting, milling, grinding and etching.

8. A method in accordance with claim 6, wherein a height of at least one larger and one smaller tooth of the tooth period pattern is determined, wherein the height of the larger tooth and the height of the smaller tooth are determined starting from a common tooth tip line.

9. A method in accordance with claim 6, wherein a protector lip extends in a circumferential direction at said distal end of said milling cutter shaft, said protector lip extending between one of said plurality of teeth and another one of said plurality of teeth, said protector lip extending in an axial direction of said milling cutter shaft, said protector lip having an end portion, said end portion being located at a spaced location from each of said plurality of teeth in said axial direction.

10. A method of claim 6, wherein, when determining the desired tooth period length from the desired tooth height of the milling cutter toothing, a length of the larger tooth of the tooth period pattern is determined such that the length of the larger tooth is ⅔ of a tooth height and a length of the smaller tooth of the tooth period pattern is determined such that the length of the smaller tooth is ⅓ of a tooth height, wherein the tooth period length corresponds to a sum of lengths of the teeth.

11. A method for manufacturing a bone milling cutter, wherein a milling cutter toothing is created at a distal face of a tubular milling cutter shaft of a bone milling cutter and at a given outer diameter of a milling cutter shaft, the method comprising the following steps, executed in sequence:
a) determining a tube circumference of the milling cutter shaft;
b) ascertaining an average desired tooth height of the milling cutter toothing;
c) ascertaining a desired tooth period length of the milling cutter toothing from the desired tooth height at given parameters for a tooth period pattern;
d) dividing the tube circumference by the desired tooth period length and rounding the results to an even number value;
e) dividing the tube circumference by the even number value to obtain an actual tooth period length; and
f) mechanically removing or severing material at the distal end of the milling cutter shaft to configure previously determined milling cutter toothing via one of laser cutting, grinding, milling and etching, said tooth period pattern containing at least one pair of teeth, wherein a height of at least one larger and one smaller tooth of the tooth period pattern is determined, wherein the height of the larger tooth and the height of the smaller tooth are determined starting from a common tooth tip line.

12. The method of claim 11, wherein the tube circumference is determined by an outer diameter.

13. The method of claim 11, wherein the parameters for the tooth period pattern comprise at least one wedge angle.

14. The method of claim 11, wherein the parameters for the tooth period pattern comprise at least one angle of incidence.

15. The method of claim 11, wherein a fraction of the tooth period length is formed to determine a length of at least one tooth of the tooth period pattern.

16. The method of claim 11, wherein a fraction of the tooth height is formed to determine a height of at least one tooth of the tooth period pattern.

17. The method of claim 11, wherein a length of the at least one larger and one smaller tooth of the tooth period pattern is determined.

18. The method of claim 17, wherein, when ascertaining the desired tooth period length from the desired tooth height of the milling cutter toothing, a length of the larger tooth of the tooth period pattern is determined such that the length of the larger tooth is ⅔ of a tooth height and a length of the smaller tooth of the tooth period pattern is determined such that the length of the smaller tooth is ⅓ of a tooth height, wherein the tooth period length corresponds to a sum of lengths of the teeth.

19. The method of claim 11, wherein, when ascertaining the desired tooth period length from the tooth height of the milling cutter toothing, a length of the larger tooth of the tooth period pattern is determined such that the length of the larger tooth is ⅗ of the desired tooth height and a length of the smaller tooth of the tooth period pattern is determined such that the length of the smaller tooth is ⅖ of the tooth height, wherein the tooth period length corresponds to a sum of the lengths of the teeth.

20. A method in accordance with claim 11, wherein said distal end of said milling cutter shaft comprises a plurality of teeth and a protector lip extending in a circumferential direction at said distal end of said milling cutter shaft, said protector lip extending between one of said plurality of teeth and another one of said plurality of teeth, said protector lip extending in an axial direction of said milling cutter shaft, said protector lip having an end portion, said end portion being located at a spaced location, in said axial direction, from each of said plurality of teeth.

* * * * *